(12) United States Patent
Shen et al.

(10) Patent No.: US 6,180,378 B1
(45) Date of Patent: Jan. 30, 2001

(54) IMMOBILIZATION OF BIOACTIVE PROTEIN IN PHYLLOSILICATES

(75) Inventors: Siyuan Shen, Wyndmoor; An-Fei Hsu, Ambler; Thomas A. Foglia, Lafayette Hill; Shu-I Tu, Warrington, all of PA (US)

(73) Assignee: The United States of America as represented by the Secretary of Agriculture, Washington, DC (US)

( * ) Notice: Under 35 U.S.C. 154(b), the term of this patent shall be extended for 0 days.

(21) Appl. No.: 09/239,778

(22) Filed: Jan. 29, 1999

(51) Int. Cl.$^7$ .......................... C12N 11/14; C12N 11/04; G01N 33/552; C07K 17/14
(52) U.S. Cl. .......................... 435/176; 435/182; 436/527; 530/402; 530/811
(58) Field of Search .................................. 435/174, 176, 435/182; 436/527; 530/402, 811

(56) References Cited

PUBLICATIONS

Shen et al., *Applied Biochemistry and Biotechnology*, vol. 69, pp. 79–90, 1998.
Heichal–Segal et al., *Biotechnology*, vol. 13, pp. 798–800, 1995.
Shtelzer et al., *Biotechnology and Applied Biochemistry*, vol. 15, pp. 227–235, 1992.
Spring et al., *Chemical Abstracts*, 250683r, vol. 123, p. 534, 1995.
Janowski et al., *Chemical Abstracts*, 131360e, p. 351, vol. 110, 1989.
Battu et al., *Biochimica et Biophysica Acta*, 1211, pp. 270–276, 1994.

*Primary Examiner*—David M. Naff
(74) *Attorney, Agent, or Firm*—M. Howard Silverstein; John D. Fado; Janelle S. Graeter

(57) ABSTRACT

Immobilized bioactive protein compositions are prepared containing a bioactive protein such as an enzyme intercalated into galleries of a phyllosilicate, and a crosslinking compound crosslinking the phyllosilicate and the bioactive protein. The phyllosilicate may contain sodium or alkylammonium ions and be montmorillonite. The protein may be lipoxygenase, and crosslinking compounds include tetramethyl orthosilicate, tetraethoxy silicate, propyltrimethoxy silicate, polydimethylortho silicate and methyltrimethoxy silicate. The composition is prepared by delaminating a sodium-saturated phyllosilicate, mixing a bioactive protein with the delaminated phyllosilicate and crosslinking with a crosslinking compound. After crosslinking, the composition may be vacuum dried and ground. The composition can also be prepared by delaminating a montmorillonite, saturating the delaminated montmorillonite with sodium ions, mixing the resultant montmorillonite with an enzyme, adding tetramethyl orthosilicate, allowing crosslinking, and drying. Activities of up to 170% of free protein are achieved using the immobilized bioactive protein compositions, and the compositions retain up to 98% original activity after being stored at room temperature for two weeks.

21 Claims, 6 Drawing Sheets

IMMOBILIZATION OF BIOACTIVE PROTEIN IN PHYLLOSILICATES

BACKGROUND

Lipoxygenase (LOX) enzymes are useful in the oxidation of fatty acids for a variety of commercial purposes. Peroxidases (POD) are oxidoreductases with many applications in medical, environmental and industrial processes including removing aromatic amines or phenols from water by peroxidase-catalyzed transformation (Klibanov, A. M. and Morris, E. D. [1981] *Enzyme Microb Technol.* 3:119; Klibanov, A. M. et al. [1983] *Science* 221:259). Immobilized peroxidases have been used in biosensors to detect pesticide residues (Sandberg, R. G. et al. [1992] *Biosensor design and application*, Mathewson, P. R. and Finley, J. W. eds., ACS, Washington D.C., pp. 81–88).

Labile proteins such as lipoxygenases, peroxidases and lipases lose most of their activity in aqueous solutions quickly. Immobilizing the enzyme would enable a continuous process that gives high substrate conversions, good product recovery, and minimal loss of enzyme activity. Conventional methods of enzyme immobilization include covalently binding or adsorbing the enzymes onto a solid support. LOX has been immobilized by adsorption to glutenin, gliadin, glass wool, talc, polymer beads, and ion-exchange supports (Cuperus, F. P. et al. [1995] *Catalysis Today* 25:441–445; Battu, S. et al. [1994] *J. Agric. Food Chem.* 42:2115–2119). The matrices used in covalent binding of LOX include oxirane acrylic beads, CNBr-activated sepharose and agarose, and carbonyidi-imidazole-activated polymer (Parra-Diaz, D. et al. [1993] *Biotech. Appl. Biochem.* 18:359–367). Although improving the stability of the enzyme, covalent and ionic bonds formed by these methods can cause a decrease in enzyme activity. For example, the adsorption of *S. tuberosum* lipoxygenase on talc retained only 53% of its activity in immobilized form (Battu et al., supra). Immobilization of enzymes by entrapment has been achieved by encapsulating enzymes through sol-gel processes (Avnir, D. et al. [1994] *Chem. Mater.* 6:1605–1614). The entrapped enzymes retained much of their activity and had better stability in the sol-gel matrices. Extension of this technique, however, was limited by two shortcomings of sol-gel materials: their brittleness and narrow pore network (Heichal-Segal et al. [1995] *Biotechnology* 13:798–800). Efforts were made to improve the activity of immobilized enzymes by introducing matrix-relaxing additives, such as algenate or polymers (Heichal-Segal et al., supra; Shtelzer, S. et al. [1992] *Biotech. Appl. Biochem.* 15:227–235) into sol-gel matrices, or mixing alkyl-substituted silanes in a specific ratio (Reetz, M. T. et al. [1996] *Biotechnol. Bioengineering* 49:527–534). Despite these improvements, however, efficient alternative methods are still needed for enzyme immobilization to provide high activity and increased storage stability. Most methods for immobilizing LOX provide materials that are not stable longer than about a month at room temperature. The best immobilization methods in the literature, based on the covalent binding or adsorption of lipoxygenases, typically immobilize lipoxygenases to 70% of protein content with about 50% retainment of enzyme activity.

Clay minerals are naturally occurring phyllosilicates (i.e., layered silicates) with good intercalative properties. Because their layered structures can be broken down into nanoscale building blocks, phyllosilicates can serve as a framework for intercalation. Metal hydroxyl polymeric cations, alkylammonium ions, polymers, and their combinations have been intercalated into phyllosilicates to form a broad spectrum of materials ranging from pillared clays and organoclay, to polymer-clay nanocomposites. The intercalated phyllosilicates exhibit good mechanical and thermal stability, controlled pore size (0.2–1 $\mu$m) and ion mobility, and high adsorption capacity. (Monnier, A. et al. [1993] *Science* 261:1299–1303; Pinnavia, T. J. [1983] *Science* 220:365–371; Vaia, R. A. et al. [1994] *Chem. Mater.* 6:1017–1022; Yan, Y. and Bien, T. [1993] *Chem. Mater.* 5:905–907; and Burnside, S. D. and Giannelis, E. P. [1995] *Chem. Mater.* 7:1597–1600.)

Compositions providing highly active immobilized bioactive proteins which are storage-stable are needed, as are efficient methods for producing such compositions.

All publications referred to herein are incorporated by reference to the extent not inconsistent herewith.

SUMMARY

This invention provides compositions comprising active, immobilized bioactive proteins, said compositions comprising a phyllosilicate, a bioactive protein intercalated into the galleries of the phyllosilicate, and a crosslinking compound crosslinking said phyllosilicate and said bioactive protein. Activities of up to 170% of free protein are achieved using the immobilized bioactive protein compositions of this invention. The compositions also provide excellent storage stability, retaining up to 98% original activity after being stored at room temperature for two weeks.

Immobilized bioactive proteins, including enzymes such as lipoxygenase, have many commercial uses. For example, lipoxygenases can be used to catalyze the oxidation of polyunsaturated fatty acids containing a Z-1, Z-4 pentadiene structure to give a Z-1, E-3 conjugated diene-5-monohydroperoxy derivative. Reduced derivatives of these hydroperoxy compounds can serve as replacements for ricinoleic acid and hence are useful in a number of industrial applications as lubricants, grease thickeners and drying oils. Currently ricinoleic acid is obtained from caster oil, a commodity that is imported into the United States at a level of thirty thousand metric tons per year. Hydroperoxy fatty add derivatives can be exploited as chemical synthons in pharmaceutical and chemical applications. For example, the perhydroxy derivatives of arachidonic acid serve as precursors in the synthesis of prostaglandins and leukotrienes. The hydroperoxy derivates of linoleic and linolenic acid are useful as fungicides in agricultural applications.

Phyllosilicates are layered silicates and include many naturally-occurring clay minerals such as montmorillonite, vermiculite, illite, mica and kaolinite, and synthetic phyllosilicates such as talc.

Sodium ions or other cations can be used to saturate the phyllosilicate in order to delaminate the phyllosilicate. Any cation not causing significant collapse of the phyllosilicate structure can be used, but sodium is preferred. Alkylammonium ions can be used to replace the sodium ions to make the phyllosilicate more hydrophobic. Hydrophobicity aids in immobilization of bioactive proteins such as lipoxygenase (LOX), Lipase PS30, Lipase SP523 and HPOD lyase, and other such proteins. However, for proteins such as peroxidase (POD) hydrophobicity is undesirable, and the sodium-ion-substituted phyllosilicates work best. Optimization of treatment of the phyllosilicate with alkylammonium after sodium ion delamination can be routinely done depending on the bioactive protein used.

The alkylammonium ion used may have any alkyl group known to the art as a substituent. Preferred alkylammonium ions include trimethylammonium (TMA) and cetyltrimethylammonium (HDTMA). Larger alkyl groups will make the composition more hydrophobic. Hydrophobicity of the composition can be adjusted by selecting alkylammonium ions to optimize the material for specific enzymes by those skilled in the art without undue experimentation.

The bioactive protein (also referred to herein as a biologically active protein) is any protein capable of reacting with another molecule (referred to herein as the "substrate") in a desired reaction. Enzymes are a preferred class of bioactive protein in this invention. Preferred enzymes include lipoxygenase, peroxidase, trypsin, acid phosphatase, β-glucosidase, lipase, alkaline phosphatase, hydroxylase, reductase and superoxide dismutase. Other suitable bioactive proteins include albumin and cell-bounded enzymes on living cells, antibodies and bacteria.

The crosslinking compound is any compound capable of reacting with the phyllosilicate material to form traps for the bioactive protein, such that the crosslinking compound and phyllosilicate materials are linked together in a polymeric, crosslinked material. A preferred crosslinking compound is tetramethyl orthosilicate (TMOS). Other suitable crosslinking compounds are known to the art and include alkyl silicates such as tetraethoxy silicate, propyltrimethoxy silicate, polydimethyl orthosilicate and methyltrimethoxy silicate.

The composition of this invention is a solidified material having a pore size large enough to allow substrate diffusion and small enough to constrain the trapped bioactive proteins. Preferably the pores are smaller than or equal to about 2 $\mu$m, and more preferably they are smaller than or equal to about 0.5 $\mu$m. The composition preferably has a macroporous structure, i.e. pore size greater than about 0.13 $\mu$m.

The crosslinked material is used in dry form, and is preferably dried by a procedure such as room-temperature vacuum drying or air drying which allows it to remain sufficiently hydrated so that the macropores do not collapse. Freeze drying generally removes so much water that the macroporous structure is damaged.

The composition must contain sufficient crosslinking compound to solidify the material, but not so much as to harm the activity of the trapped bioactive protein.

With lipoxygenase as the bioactive protein, montmorillonite as the phyllosilicate saturated with trimethylammonium ions, and tetramethyl orthosilicate as the crosslinking compound, activities of 170% of that of free lipoxygenase are achieved.

This invention also provides methods of making such compositions comprising bioactive proteins immobilized in phyllosilicates comprising:

(a) delaminating a phyllosilicate;

(b) mixing the bioactive protein with the phyllosilicate; and (c) crosslinking the phyllosilicate and the bioactive protein with a crosslinking compound.

The phyllosilicate is delaminated by dispersal in water and, preferably also saturating with sodium ions.

As discussed above, the method may also include replacing the sodium ions in the delaminated phyllosilicate with alkylammonium ions. When alkylammonium ions are used, they may be added to the phyllosilicate material prior to adding the bioactive protein or at the same time, but preferably prior to adding the bioactive protein.

An aqueous suspension of the phyllosilicate containing between about 1% and about 3% w/v is formed. Saturation with sodium or other useful cation causing delamination is done by washing with a solution of the salt of the desired cation until the phyllosilicate is substantially saturated. A solution of an alkylammonium salt is preferably then used to replace the sodium ions with alkylammonium ions. The alkylammonium solution is preferably used at a concentration of between about 0.5 M and about 1 M to supply sufficient alkylammonium ion to replace substantially all the delaminating ions. The crosslinking compound is then added to the phyllosilicate at a volume ratio of phyllosilicate suspension to crosslinking compound of between about 1:1 and about 20:1, preferably between about 5:1 and about 10:1.

The method also includes drying the material, preferably vacuum or air drying under conditions, e.g. room temperature, not leading to complete dehydration or substantial collapse of the microporous structure of the material. The material may then be ground for use. The particles of the material are colloidal in size.

GLOSSARY

CEC: cation exchange capacity
CHS: cetyltrimethylammonium-treated montmorillonite
CS: montmorillonite in which sodium ions have not been replaced
CTS: trimethylammonium-treated montmorillonite
HDTMA: cetyltrimethylammonium chloride
HPOD: hydrogen peroxidase
LA: linoleic acid
LOX: lipoxygenase
MPOD: mobilized peroxidase
MTMS: methyltriethoxysilane
POD: peroxidase
$R_v$: volumetric ratio
S: silicate sol-gel matrix
SEM: Scanning Electron Microscopy
SWy-1: a montmorillonite
TMA: trimethylammonium chloride
TMOS: tetramethyl orthosilicate

DETAILED DESCRIPTION

Figure 1:
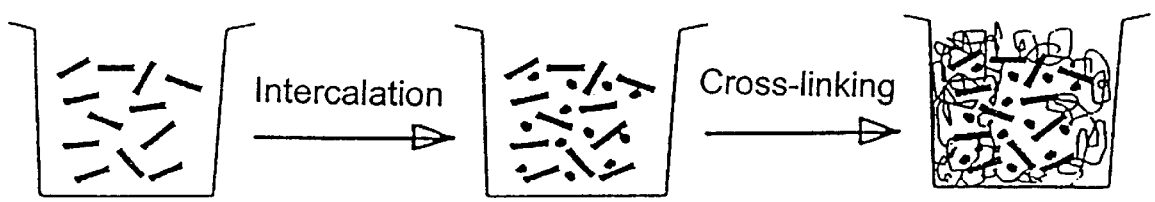
FIG. 1 is a schematic diagram showing intercalative immobilization of bioactive proteins in crosslinked phyllosilicates.
Figure 2:
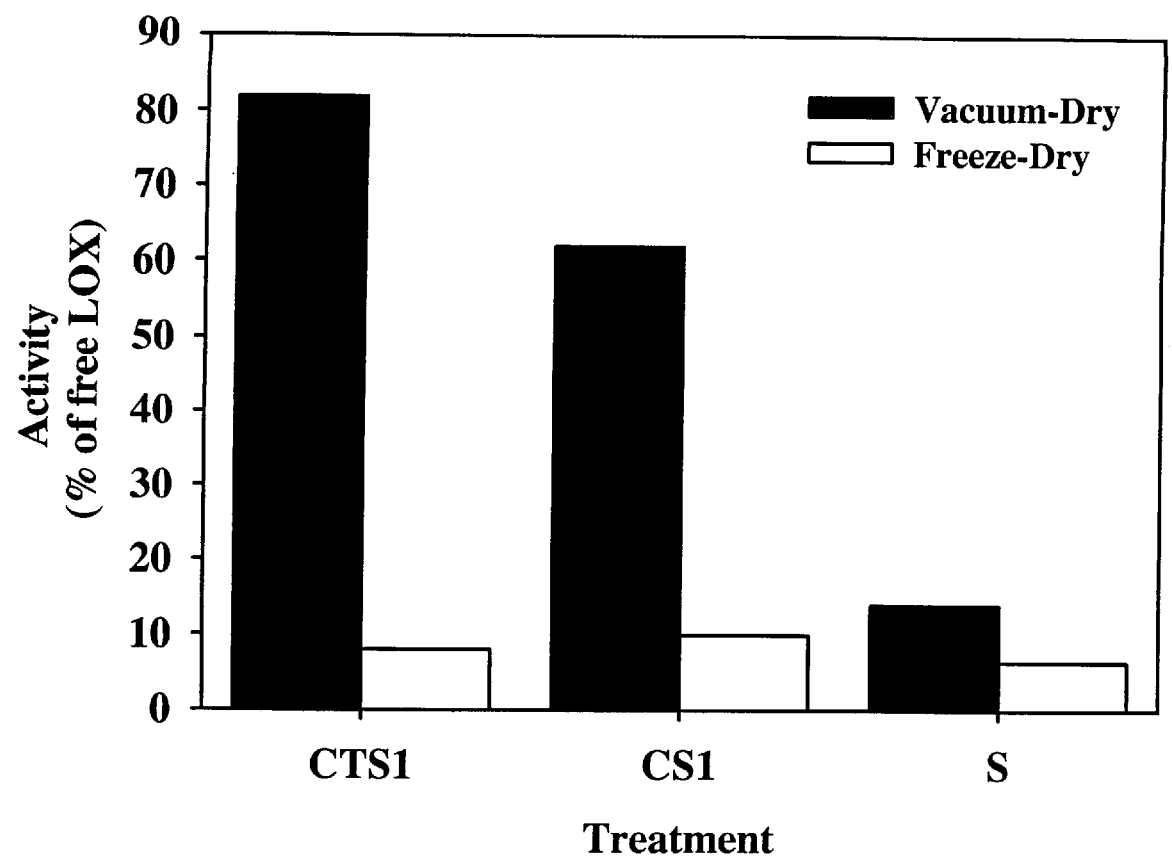
FIG. 2 is a graph comparing the activity of lipoxygenase (LOX) intercalated in montmorillonite in which sodium ions have been replaced with alkylammonium ions (CTS); LOX intercalated in montmorillonite in which sodium ions have not been replaced (CS); and LOX entrapped in silicate sol-gel matrix (S). Comparison of the foregoing compositions treated either by vacuum drying (vertically striped bars) or freeze drying (horizontally striped bars) is also shown.

The use of phyllosilicates such as montmorillonite for immobilization of biologically active proteins provides enhanced storage stability and reusability with activities as good as or better than free protein. The phyllosilicate is delaminated by suspension in water and saturation with sodium ions. Optionally, the delaminated phyllosilicate suspension is treated with an alkylammonium composition such as tetramethyl ammonium chloride (TMA) or cetyltrimethylammonium chloride (HDTMA) to replace sodium ions with alkyl ammonium ions. The suspension is then contacted with the biologically active protein, e.g. lipoxygenase (LOX) or peroxidase (POD), and a crosslinking agent such as tetramethyl orthosilicate (TMOS) is added. If desired a small amount of sodium fluoride or other salt may be added to catalyze the crosslinking reaction. After sufficient time, e.g. overnight, is allowed for polymerization, a particulate macroporous material is formed with biologically active protein intercalated in the galleries (spaces between the layers) of the phyllosilicate and available for reaction with a desired substrate. The composition may be neutralized by washing with buffer, and dried by means which preserve the macroporous structure and do not significantly denature the protein. Both freeze-drying and vacuum-drying may be used to remove water after the immobilization treatments. In the course of experimentation it was found that the vacuum-dried samples retained much of their enzymatic activity, whereas the freeze-dried samples lost most of their activity (FIG. 2). The phyllosilicate suspended in buffer solution served as the framework and introduced macropores (0.2–1 µm) to the composite. Vacuum drying removed excess water from the composites but still kept them in a hydrated state, which preserved the original structure of the composite. In contrast, freeze-drying removed most of the water from the composites, causing the samples to shrink, presumably by collapse of the framework. This shrinkage of the silicate framework, along with dehydration of the protein, might cause denaturing of the intercalated LOX. Accordingly, samples were vacuum-dried in all subsequent experiments. Since air-drying required longer time than vacuum drying and since both exhibited an activity similar to that of the new enzyme, vacuum drying was preferred in experiments.

The dried material may be used to provide biologically active protein for reaction with a substrate, preferably a solution or suspension capable of diffusion into the pores thereof. Previous work by Piazza et al. (*Biotechnol. Appl. Biochem.* [1994] 19:243–252) indicated that 1,3-dilinolein was the poorest substrate for the oxidation reaction catalyzed both by free LOX and LOX covalently immobilized on a polymer. In contrast, we reported that LOX immobilized in sol-gel matrix oxidized 1,3-dilinolein at 93% of linoleic acid. From this study and the work on LOX immobilized in sol-gel matrix, it appears that LOX immobilized by entrapment methods has a higher substrate preference for 1,3-dilinolein compared to the oxidation reaction catalyzed by free LOX or covalently linked LOX. As the macropores in the structure are important for allowing diffusion of substrate, which may be liquid or may be a solid in solution or suspension, into the material for contact with the biologically active protein, complete drying of the material resulting in collapse of the macropores is not desirable. The material may be stored for periods of up to three months or longer while maintaining excellent activity, and generally provides better storage stability than free biologically active protein. In immobilized form on the phyllosilicate, the biologically active protein may be used two or three times.

Immobilization of bioactive proteins on phyllosilicate materials provides better activity than immobilization in sol-gel materials of the prior art, due at least in part to better diffusion of the substrate into the material. As shown below, the use of phyllosilicates improves substrate diffusion by introducing macropores into the composites but failed to eliminate all limits on substrate diffusion to the immobilized enzymes. This was noted since the activity of the ground samples was higher than that of nonground samples from the same preparation (Table 1). Reaction speeds are comparable to those of free biologically active protein.

In addition, it is known that the deactivation of the LOX reaction is due to product inhibition, MPOD accumulation and partial anaerobic conditions that develop during the reaction (Siedow, J. N. [1991] *Ann. Rev. Plant Physiol Plant Mol. Biol.* 42:145–188). To study reaction kinetics, the amount of protein used in the experiment has to be small enough to avoid the inhibition. In a previous study, it was found that when LOX was immobilized in the sol-gel matrix, the oxidation reaction was less sensitive to MPOD inhibition. Therefore, the immobilized state of the enzyme remains active longer than the free enzyme.

An interesting aspect of these lipoxygenase-phyllosilicate composites is that the composites after silicate polymerization behave like frozen suspensions of LOX and the phyllosilicate. The LOX, after intercalation into dispersed phyllosilicates, is restrained in the galleries (i.e., interlayers) of phyllosilicates, yet the intercalated LOX was shown to be relatively free from tight binding with phyllosilicates that were pretreated with organic counter ions, e.g., TMA, and this treatment with organics was helpful in retaining enzymatic activity. Another interesting effect is the stimulation caused by the addition of isooctane as reported by Parra-Diaz et al. (*Biotech. Appl. Biochem.* [1993] 18:359–367). In that study, the addition of 35% isooctane to the reaction mixture resulted in a 3-fold increase in LA oxidation rate as compared to the reaction without the addition of isooctane. LOX was immobilized by covalent linkage to carbonyl-di-imidazole-activated polymer and in the present study, LOX is entrapped in phyllosilicates. It appears that the addition of isooctane increases the oxidation rate of LA for all types of immobilized LOX. We also found a similar solvent effect occurred in the oxidation reaction catalyzed by LOX immobilized in a sol-gel matrix. In that study, the oxidation rate was also increased (about 40% stimulation) compared to the reaction in the absence of isooctane.

The interactions between enzymes and phyllosilicates may include electrostatic interaction, hydrogen bonding, hydrophobic adhesion, or covalent bonding (Cuperus et al.

[1995] supra; Messing, R. A. [1976] in Immobilized Enzymes, Part A, K. Mosbach ed., *Methods Enzymol.* 44:148–183). Electrostatic interactions between external charges on enzymes and phyllosilicates is the primary force governing adsorption. Factors controlling immobilization by electrostatic adsorption include active sites, pH, ionic strength, and relative amounts of enzyme and phyllosilicate (Battu et al. [1994] supra; Messing, R. A. [1976] supra; Arseguel, D. and Baboulene, M. [1995] *Biocatal. Biotransform.* 12:267–279). It is shown herein that LOX is denatured by electrostatic interactions (Table 1), whereas this effect is insignificant for peroxidases. A similar observation was found for peroxidases and lipases adsorbed on talcs (Arseguel and Baboulene [1995] supra). One possible explanation for this difference may be the locations of charge sites in the enzymes. Enzyme activity may be inhibited if the electrostatic interactions of charge sites interfere with the catalytic sites of an enzyme (Messing [1976] supra). Hydrophobic/hydrophilic balance in an immobilization matrix is another factor that can influence the catalytic activity of an immobilized enzyme (Arseguel and Baboulene [1995] supra). A strong hydrophobic matrix may tightly adsorb and inactivate enzymes, whereas no enzyme may be adsorbed onto a hydrophilic support (Cuperus et al. [1995] supra). LOX, like lipases (Arseguel and Baboulene [1995] supra), favors a hydrophobic/hydrophilic-balanced (amphiphilic) matrix because of lipophilicity. Incorporating alkylammonium ions on the phyllosilicate surface adjusts the amphiphilicity of phyllosilicates and might also disrupt hydrogen bonds, causing fast inactivation of the enzyme after it is adsorbed on the phyllosilicates (Pinnavaia, T. J. [1982] ACS *Symposium Series* 192:241–253).

In contrast, using peroxidase (POD), activity was less using TMA, as the more hydrophobic material appeared to have less preference for POD than LOX, decreased dispersion of the material in the solution containing the substrate, and caused aggregation, thus reducing the space within the phyllosilicate galleries. X-ray diffraction measurements were used to provide an estimation of the degree of phyllosilicate dispersion. Reflection peaks in the range of $2\theta=1-9°$ indicate ordered stacks of phyllosilicate layers with various spacing. The dispersion of phyllosilicates is the most important factor for intercalative immobilization of enzymes.

As shown in Table 3, another important factor influencing the activity of intercalatively immobilized POD was the volumetric ratio ($R_v$) of phyllosilicate suspension and TMOS used in crosslinking of phyllosilicates. With increasing ratio $R_v$, the activity of immobilized POD increased. This trend was the same for all phyllosilicates with different surface cations. An increase in ratio $R_v$ means a decrease in the amount of TMOS used for the same amount of phyllosilicate from 62.5 to 6.25, and an increase in the stoichiometric ratio of water to silane from 8.5 to 84 (Table 3). When immobilizing lipases in MTMS-derived gels, Reetz et al. found that optimal stoichiometry ratio of water to silane was 8 to 10 (Reetz, M. T. et al [1996] *Biotechnology & Bioengineering* 49:527–534). Below and above this region, the activity of immobilized lipases decreased. In our study, phyllosilicates provided the framework for the immobilizing matrix. TMOS was used only as a crosslinking agent. Within a range ($R_v \leq 10$), increasing the amount of phyllosilicate resulted in increasing porosity of the crosslinked phyllosilicate, which reduced the limitation on the substrate diffusion and increased the activity of immobilized POD. The attempt to use $R_v=20$ for intercalative immobilization failed because the amount of TMOS fell in short of the minimum requirement for matrix solidification.

When an alkylammonium ion is used, it can be added prior to the protein or at the same time; however, somewhat better activity appears to result from adding the alkylammonium ion prior to the protein. Use of a longer alkyl group with the alkylammonium ion (e.g. HDTMA) does not appear to affect activity of the material compared to use of a shorter alkyl group (e.g. TMA) when LOX is the biologically active protein; however, when POD is the biologically active protein, the longer alkyl group appears to adversely affect activity by causing too much aggregation. Using an amount of alkylammonium ion greater than the cation exchange capacity of the phyllosilicate material is preferred. In general, the higher the ratio of phyllosilicate to crosslinker, the better, because more frame structure is produced which has no harmful effects on enzymes, so long as sufficient crosslinker is provided to solidify the material.

The crosslinked composition forms a solid chunk and may be ground to a desired particle size for use, e.g., to pieces between about 3 mm and about 1 cm.

TABLE 1

Enzymatic Activity (% of Freshly Prepared Free LOX) of Immobilized Soybean Lipoxygenase After Vacuum-Drying

|  | Fresh-prepared free LOX | Frozen free LOX[b] | CTS1[a] | CTS2[a] | CTS3[a] | CTS4[a] | CHS[a] | CS1[a] | CS2[a] | S[a] |
|---|---|---|---|---|---|---|---|---|---|---|
| Nonground | 100 | 33.9 | 26.2 ± 2.4 | 45.9 ± 2.7 | — | — | — | 9.04 ± .6 | 3.12 ± .03 | 0.04 ± .002 |
| Ground | — | — | 31.7 ± 2.1 | 95.9 ± 5.8 | 133.5 ± 8.0 | 161.6 ± 8.5 | 152.3 ± 12.9 | 25.6 ± 1.9 | 6.47 ± .04 | 3.64 ± .03 |
| SWy-1/TMOS volume ratio | — | — | 1 | 5 | 10 | 5 | 5 | 1 | 5 | 0 |
| Buffer/TMOS volume ratio | — | — | 2 | 10 | 10 | 5 | 5 | 2 | 10 | 1 |

[a]Treatment codes: C, Clay SWy-1 (montmorillonite from Source Clay Minerals Repository, Columbia, MO); T, TMA (trimethylammonium); H, HDTMA (cetyltrimethylammonium); S, TMOS (tetramethyl orthosilicate).
[b]Free LOX in aqueous solution stored frozen for 2 days.

EXAMPLES

Example 1

Immobilization of Soybean Lipoxygenase

A lipoxygenase-phyllosilicate composite was prepared by intercalating soybean lipoxygenase into dispersed Na-, TMA-, or HDTMA-phyllosilicate, and then crosslinking the phyllosilicate with silicates from TMOS hydrolysis.

Immobilization Procedure. A phyllosilicate (montmorillonite SWy-1 from Source Clay Minerals Repository, Columbia, Mo.) was Na-saturated by three washes with 1 MNaCl solution, followed with three washes with deionized water to remove excess salt. The Na-saturated SWy-1 was fractionated for particle-size ≦2 μm and dispersed in water. The concentration of the phyllosilicate suspension was 3.3% (w/v). The Na ions were exchanged subsequently with alkylammonium ions by treatment of the Na-phyllosilicate with trimethylammonium chloride (TMA) (HN[CH$_3$]$_3$Cl) or cetyltrimethylammonium chloride (HDTMA) (CH$_3$[CH$_2$]$_{15}$ N[CH$_3$]$_3$Cl) obtained from Aldrich (Milwaukee, Wis.). The intercalation of soybean lipoxygenase (type I-B obtained from Sigma, St. Louis, Mo.) into the galleries of phyllosilicate was accomplished by mixing the enzyme with the dispersed phyllosilicate in buffer solution (0.2 M Na$_3$BO$_3$, pH 9.0). Crosslinking of enzyme-phyllosilicate mixture was accomplished by adding tetramethyl orthosilicate (TMOS) (Si[OCH$_3$]$_4$) from Aldrich to the mixture and vortexing for one minute. The volume ratios of buffer solution, phyllosilicate suspension, and TMOS are listed in Table 1. For comparison, TMOS was added to LOX in buffer solution (volume ratio 1:1) as the sol-gel treatment (Dave, B. C. et al. [1995] *Chem. Mater.* 7:1431–1433). The crosslinked enzyme-phyllosilicate complex was kept at room temperature overnight for completion of the polymerization reaction. After freeze-drying or vacuum-drying at room temperature for 24 hours, the enzyme-phyllosilicate complex was ready for use.

Measurement of Enzymatic Activity. The activity of the immobilized lipoxygenase was assayed by measurement of hydroperoxide formation (Parra-Diaz, D. et al. [1993] supra). An aliquot of the substrate (5 μmoles of linoleic acid) dissolved in methylene chloride was placed in a 10 mL flask and evaporated to dryness under a stream of nitrogen. The reaction medium containing 0.2 mL of 100 mM deoxychlorate (DOC) and 1.8 mL of sodium borate buffer (0.2 M, pH 9.0) was added to the substrate, and the mixture was then shaken at 250 rpm for 0.5 h at 15° C. The reaction was initiated by adding a suitable amount (approximately 0.15 mg) free or immobilized LOX. Oxidation was conducted at 15° C. with agitation at 250 rpm for two hours. The reaction was quenched by adding 400 μL of 1 M citric add. Linoleic acid hydroperoxide was isolated by extracting the reaction mixture twice with 2 mL chloroform:methanol (2/1, v/v). After removing the solvent under a stream of nitrogen, the hydroperoxide was redissolved in 3 mL ethanol. The amount of hydroperoxide was determined spectrophotometrically by the xylenol orange method (Jiang, T.-Y. et al. [1991] *Lipids* 26:853–856). Standards were prepared by diluting a commercial cumene peroxide. All results were corrected by subtracting the reading from controls without enzymes. All measurements were in triplicate.

Scanning Electron Microscopy (SEM). A small fragment of each sample was immersed in 1 mL 10% glutaraldehyde for protein fixation, washed in 0.1 M imidazole buffer solution, dehydrated in 50% ethanol and then pure ethanol, and frozen in liquid N$_2$ for five minutes. The frozen fragments were thawed into pure ethanol and critical-point dried from CO$_2$. A few chunks of the treated samples were glued to aluminum stubs with colloidal silver adhesive paint and coated with a thin layer of gold. The images were collected with a JSM-840A SEM at a magnification of 10,000×. The instrument conditions were 15 kV, 3×10$^{-11}$ A, and 70 μm objective aperture.

Enzymatic Activity of Immobilized LOX. LOX was efficiently immobilized in the crosslinked phyllosilicate as demonstrated by the enzymatic activity of enzyme-phyllosilicate composites. Intercalatively immobilized LOX exhibited higher activity than LOX immobilized by the simple sol-gel entrapment (FIG. 2).

For the same amount of SWy-1, LOX intercalated in the phyllosilicate saturated with TMA had higher activity than LOX immobilized in Na-saturated SWy-1 (FIG. 2). A more significant difference in LOX activity was noted between Na- and TMA-phyllosilicate with increasing amounts of phyllosilicates used for the immobilization (Table 1). For TMA-saturated SWy-1, the activity of immobilized LOX increased with the amount of phyllosilicate used (from treatment CTS1 to CTS3), whereas an opposite effect was observed for LOX immobilized in Na-saturated SWy-1 (treatment CS1 to CS2). One possible explanation for this observation is that charge-charge interactions between LOX and SWY-1 inhibited the enzyme activity. The SEM images of CS1 and CS2 were similar to those of CTS1 and CTS2, indicating pore networks for Na- and TMA-saturated SWY-1 were similar. Exchange of Na ions with TMA reduced the cation-exchange sites and thus the net charge of the phyllosilicate because TMA strongly binds to phyllosilicates. This process also increases the hydrophobicity of the phyllosilicate (Vaia, R. A et al. [1994] *Chem. Mater.* 6:1017–1022). For the same LOX/SWY-1 ratio, treatment CTS4 (Table 1) in which Na ions were exchanged with TMA ions before intercalation of the enzyme exhibited a higher enzymatic activity than treatment CTS3 in which TMA and LOX were intercalated at the same time. Compared to TMA, the long-chain alkylammonium ions, HDTMA, showed no significant difference in the effect on the activity of immobilized LOX (Table 1).

Structure of Enzyme-Phyllosilicate Composite. The inhibition of LOX activity from enzyme-phyllosilicate interaction was insignificant for the LOX intercalated in TMA-saturated SWY-1. The restriction on substrate diffused into the composites was reduced because of the increase in macropores in the composites that was observed by scanning electron microscopy (SEM). The SEM image showed uniform silicate aggregates in the form of fused globules, ranging in size between 0.05 and 0.1 μm in the sol-gel composite. The pore network formed in this composite was also in that size (micropore and mesopore, <0.13 μm) (Shtelzer et al. [1992] supra) range. On the other hand, for the crosslinked phyllosilicate, SEM images showed turbulent clay layers immersed into the silicate network with some macropores ranging in size from 0.2 to 0.8 μm between clay layers. For a larger volume-ratio of phyllosilicate suspension to TMOS liquid, SEM images clearly showed that more macropores were introduced into the lipoxygenase-phyllosilicate composite. With macropores in the enzyme-phyllosilicate composite, substrates could diffuse more easily into the composite for reaction with the immobilized. LOX Accordingly, the intercalatively immobilized LOX had higher activity when a larger volume-ratio of TMA-saturated SWy-1 to TMOS was used for immobilization (Table 1). Another possible reason for higher enzyme activity in the composites made with lower amount of TMOS might be the smaller amounts of methanol produced from TMOS hydrolysis, which denatures most enzymes.

TABLE 2

Storage Stability of the Intercalative Immobilized LOX at 4° C. or Room Temperature[a]

| Temperature (° C.) | Storage time (d) | Treatment CTS3[b] | Treatment CTS[b] | Treatment CHS[b] |
|---|---|---|---|---|
|   | 9 | 95 ± 6 | 97 ± 6 | 103 ± 6 |
|   | 15 | 77 ± 5 | 93 ± 6 | 77 ± 5 |
| 4 | 29 | 77 ± 5 | 68 ± 5 | 64 ± 5 |
|   | 91 | 46 ± 4 | 39 ± 4 | 24 ± 4 |
|   | 181 | 44 ± 9 | 25 ± 2 | 15 ± 9 |
|   | 6 | 80 ± 5 | 93 ± 6 | 85 ± 5 |
| 22 | 13 | 82 ± 5 | 94 ± 6 | 74 ± 4 |
|   | 28 | 61 ± 4 | 72 ± 4 | 68 ± 4 |
|   | 91 | 34 ± 4 | 30 ± 4 | 11 ± 3 |

[a]Residual activity: percentage of the original immobilized activity.
[b]The treatment codes are the same as those in Table 1. The volume ratios of buffer solution, phyllosilicate suspension and TMOS for the treatments are listed in Table 1.

Storage Stability and Reusability. To assess storage stability, intercalatively immobilized LOX composites were stored with or without buffer solution at different temperatures for up to three months. Stability of immobilized LOX stored in buffer solution showed no significant difference from that stored without buffer solution. Accordingly, the data for both sample sets were combined as shown in Table 2.

The effect of storage temperature on the stability of intercalatively immobilized LOX was less significant than that of LOX immobilized by other methods. Drying was the major factor that caused the immobilized LOX to lose activity during storage. This observation was more prominent at room temperature than at 4° C. By plotting the activity date vs. storage time and using regression analysis, the half-life of intercalatively immobilized LOX was estimated to be 77, 69 and 55 d for samples CTS3, CTS4, and CHS at 4° C., respectively. At room temperature, samples CTS3, CTS4, and CHS had respectively a half-life of 57, 63, and 47 d, respectively. The half-life of intercalatively immobilized LOX was similar to that of LOX adsorbed on talc at 4° C. (Battu et al. [1994] supra), but much longer than that of LOX covalently bound to carbonyldi-imidazole-activated polymer (Parra-Diaz et al. [1993] supra).

Figure 3:
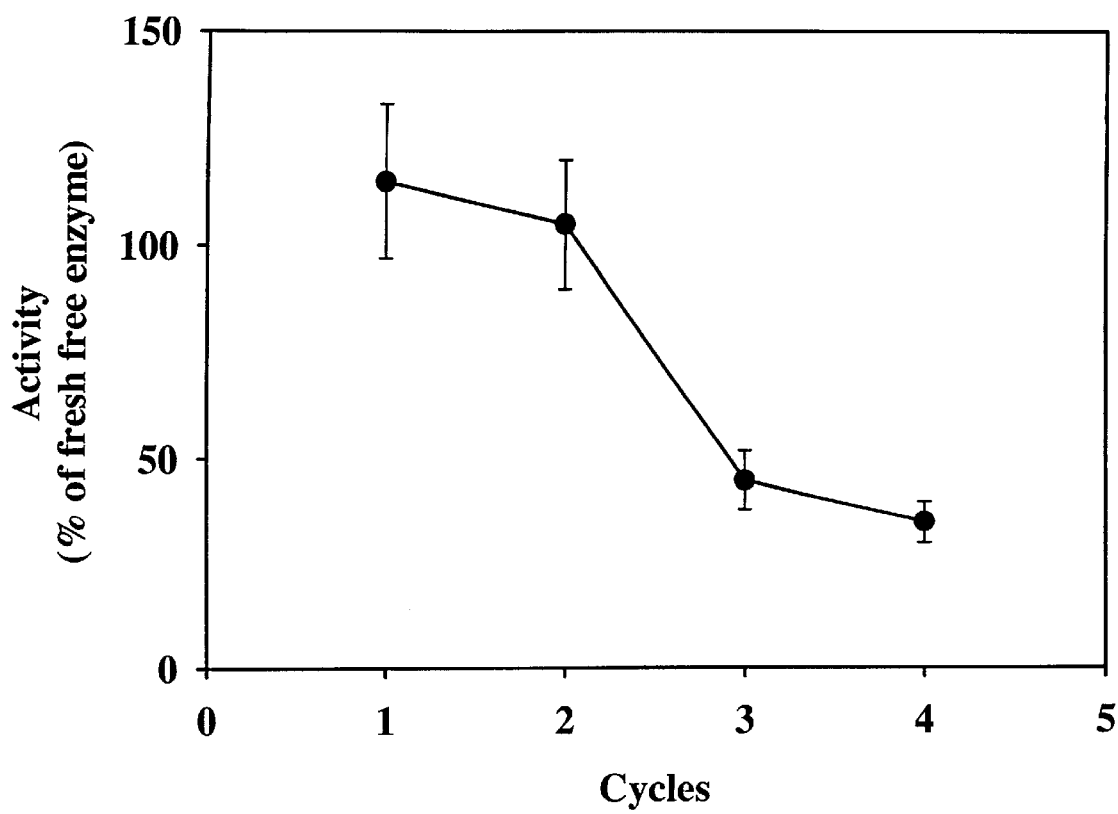
FIG. 3 is a graph showing reusability of the intercalatively immobilized LOX in montmorillonite treated with trimethylammonium chloride (TMA) to replace sodium ions, and crosslinked with tetramethyl orthosilicate (TMOS) at a ratio of montmorillonite to TMOS of 5:1.

The reusability of intercalatively immobilized LOX was evaluated by repeating incubation cycles with the substrate solution. After each cycle, the substrate solution was removed for hydroperoxide analysis and the immobilized LOX samples were washed and stored in buffer solution (0.2 M $Na_3BO_3$). The results showed that immobilized LOX retained most of its activity for the second cycle (FIG. 3), but after the third cycle, the activity decreased to approximately 30% of the original immobilized activity. The activity of the fourth cycle was still 33% of freshly prepared, free LOX. The breakdown of lipoxygenase-phyllosilicate composites had little effect on their reusability. Leaching of immobilized LOX from the enzyme-phyllosilicate composite seemed to be the major reason for the decrease in activity after the third cycle. In the leaching test, the enzyme-phyllosilicate composite was incubated in deionized water, 0.2 M $Na_3BO_3$ buffer solution, or the substrate solution used in LOX assay, and shaken at 70 rpm for 24 hours. After centrifuging, the protein content of the incubation solution was measured by Lowry assay. Depending on the type of incubation solutions, 2–6% of total immobilized protein leached out during incubation.

Example 2

Process Parameters for Use of Immobilized Lipoxygenase

In this study, lipoxygenase was immobilized in dispersed phyllosilicate layers which were crosslinked with silicate polymers formed by the hydrolysis of tetramethyl orthosilicates (TMOS) as described in Example 1. The effect of substrate concentration, reaction temperature and solvent participation were studied on the LOX oxidation of linoleic acid (LA). The temperature optimum for the oxidation of LA by immobilized LOX was 25° C. and values of $K_m$ and $V_{max}$ for this reaction were 1.7 mmoles/L and 0.023 μmoles per minute, respectively. Enzymatic activity was stimulated by the addition of 10% isooctane to the reaction mixture. The immobilized LOX preparation showed a degree of substrate preference which demonstrated that 1,3-dilinolein was a better substrate than LA in the oxidation reaction, followed in order by: 1-monolinolein, methyl oleate and trilinolein. In general, LOX immobilized in crosslinked phyllosilicates retained the physical and chemical characteristics of free LOX.

Effect of substrate concentration. The rate of hydroperoxide (HPOD) formation was measured at linoleic acid concentrations ranging from 0–20 μmoles. Higher LA concentrations were not used to avoid HPOD inactivation of the enzyme. LA oxidation catalyzed by LOX immobilized in crosslinked phyllosilicates with HPOD formation increased with increasing LA concentration. The Lineweaver-Burk plot was linear, demonstrating that the reaction follows Michaelis-Menten kinetics. Kinetic constants estimated for $K_m$ and $V_{max}$ are 1.7 mmoles/L and 0.023 μmoles/min respectively. Under similar conditions the $K_m$ and $V_{max}$ values of free LOX are 2.5 mmoles/L and 0.056 moles/min respectively. Results of analysis of $K_m$ in terms of substrate affinity for the active sites of LOX imply that when the enzyme is immobilized, it still retains its affinity for linoleic acid, but compared to free LOX, $K_m$ and $V_{max}$ values were decreased when the enzyme was immobilized in crosslinked phyllosilicate.

Temperature dependency of oxidation of LA by immobilized LOX crosslinked with phyllosilicates. The enzymatic activity of LOX immobilized in crosslinked phyllosilicates was studied over the temperature range of 0–50° C. Results showed that the optimal temperature for oxidation of LA by this immobilized LOX preparation was 25° C., which is also the optimal temperature for free LOX. In contrast to our results, previous studies (Parra-Diaz, D. et al. [1993] Biotech. Appl. Biochem. 18:359–367) that used LOX covalently linked to a carbonyl di-imidazole-activated polymer indicated that the maximum production of HPOD was at 15° C. The authors suggested that the decreased yields of HPOD at temperatures above 15° C. was a result of decomposition of HPOD or anaerobic conditions caused by decreased oxygen solubility at higher temperatures. In the present study, all buffers used in the experiments were presaturated with oxygen which could account for the shift to a higher optimum reaction temperature (15° C. to 25° C.). Another reason for the difference in optima could be the different immobilization methods used. Our study indicated that the HPOD product generated during the oxidation reaction at 25° C. did not undergo significant decomposition.

Influence of isooctane concentration on HPOD formation. The enzymatic activity of LOX immobilized in crosslinked phyllosilicate was examined at 25° C. in the reaction mixtures containing isooctane and aqueous buffer. Maximum oxidation of LA occurred in the reaction mixture containing 15% isooctane. At this level of isooctane concentration, the rate of HPOD formation was about 3.5-fold greater than in the reaction without the addition of isooctane. The rate of LA oxidation decreased at isooctane concentrations higher or lower than 15%. When free LOX was used to catalyze the oxidation of linoleic acid, HPOD production increased about two-fold with the addition of 25–30% of isooctane.

Substrate specificity for LOX immobilized in crosslinked phyllosilicates. Soybean lipoxygenase type 1-B (LOX), linoleic acid (LA), 1-monolinolein, 1,3-dilinolein and trilinolein were obtained from Sigma (St. Louis, Mo.). Relative rates of the immobilized LOX-catalyzed oxidation reactions for linoleic acid and acylglycerols containing linoleoyl residues were determined using the Xylenol Orange method (Jiang, T.-Y et al. [1991]Lipids 26:853–856) using the substrates, LA methyl ester, 1-monolinolein, 1,3-dilinolein and trilinolein. Oxidation rates were normalized to the LA oxidation rate (LA 100%). The data show that 1,3-dilinolein is oxidized to a greater extent than LA (40% more), LA methyl ester and 1-monolein were oxidized at a rate of 60% of linoleic acid, and trilinolein was oxidized at a rate 40% that of LA. In a similar study using free LOX, linoleic acid was the best substrate with trilinolein being the poorest (18% of linoleic acid). Relative substrate oxidation production by free LOX followed a similar order as that of immobilized LOX crosslinked with phyllosilicates.

Example 3

Immobilization of Peroxidase in Phyllosilicates

A phyllosilicate of 2:1 layer type (montmorillonite from Wyoming, SWy-1) was obtained from Source Clay Minerals Repository (Clay Mineral Society, Columbia, Mo.). The cation exchange capacity (CEC) of this phyllosilicate was 0.764 mol kg$^{-1}$ and the surface area 756×10$^3$ m$^2$ kg$^{-1}$ (Van Olphen, H. and Fripiat, J. J. [1979] *Data handbook for clay materials and other non-metallic minerals*, Pergamon Press, Oxford, England; Rytwo, G. et al. [1995] *Soil Sci. Soc. Am. J.* 59:554). The phyllosilicate was Na-saturated by three washes with 1 M NaCl solution, followed with three washes with deionized water to remove excess salt. The Na-saturated SWy-1 was fractionated for particle-size $\leq 2$ $\mu$m or $\leq 0.5$ $\mu$m and dispersed in water. The concentration of SWy-1 in the suspension was 3.3% (w/v).

An aliquot of phyllosilicate suspension was added to a glass tube. In some experiments, Na$^+$ ions were exchanged with alkylammonium ions by treatment of the Na-phyllosilicate with trimethylammonium chloride (TMA, Aldrich) or cetyltrimethylammonium chloride (HDTMA, Aldrich). The intercalation of horseradish peroxidase (POD) (EC 1.11.1.7, type I from Sigma, St. Louis, Mo.) into the galleries (i.e., interlayers) of phyllosilicates was accomplished by mixing the enzyme with the dispersed phyllosilicate in buffer solution (0.1 M sodium citrate-phosphate, pH 7.0). The crosslinking of the enzyme-phyllosilicate mixture was initiated by adding tetramethyl orthosilicate (TMOS, Aldrich) to the mixture, and vortexing the tube for one minute to obtain a uniform mixture for silicate polymerization. A small amount of sodium fluoride or other salts can be added as catalysts for TMOS hydrolysis. The volume ratio of buffer solution to phyllosilicate suspension was 1:1 (v/v). The weight ratio of POD to phyllosilicate was 0.006 (w/w). For comparison, the simple sol-gel immobilization preparation (Dave, B. C. et al. [1995] *Chem. Mater.* 7:1431) was made by mixing TMOS with buffer solution (volume ratio 1:1) containing the same amount of POD as other preparations. The crosslinked enzyme-phyllosilicate complex was left to stand at room temperature overnight for completion of the polymerization reaction. After vacuum-drying for 24 hours or air-drying for 48 hours at 23° C., the enzyme-phyllosilicate composite was shaken with 10 mL of sodium citrate-phosphate solution (0.1 M, pH 7.0) for 24 hours, then centrifuged and washed with deionized water. After drying for 24 hours at 23° C., the immobilized POD was ready for use. The enzyme and reagents were used as received without further purification.

Activity of free and immobilized POD was determined by oxidation of guaiacol (Bergmeyer, H. U. et al. [1983] in *Methods of enzymatic analysis*, 3$^{rd}$ Ed. Vol. 2 pp. 267–268, Verlag Chemie, Weinheim, Germany). The reaction mixture (2 mL) contained 0.5 mM guaiacol (Aldrich), 0.5 mM H$_2$O$_2$, 0.1 M Na citrate-phosphate buffer (pH 7.0), and a suitable amount of free or immobilized POD. The reaction was followed by absorbance increase at 436 nm ($\epsilon_{436\ nm}$=25.5 mM$^{-1}$cm$^{-1}$). One unit was defined as the amount of POD that oxidized 1 $\mu$mol of guaiacol in one minute at 24° C. and pH 7.0. Relative activity was compared on the basis of the same protein amount for both free and immobilized POD. Protein content of POD in solution was measured by Lowry assay and the protein content of immobilized POD was calculated as the difference between the total added enzyme protein and the protein content in solutions after immobilization. All measurements were in replicates of 3 or 5.

Figure 4:
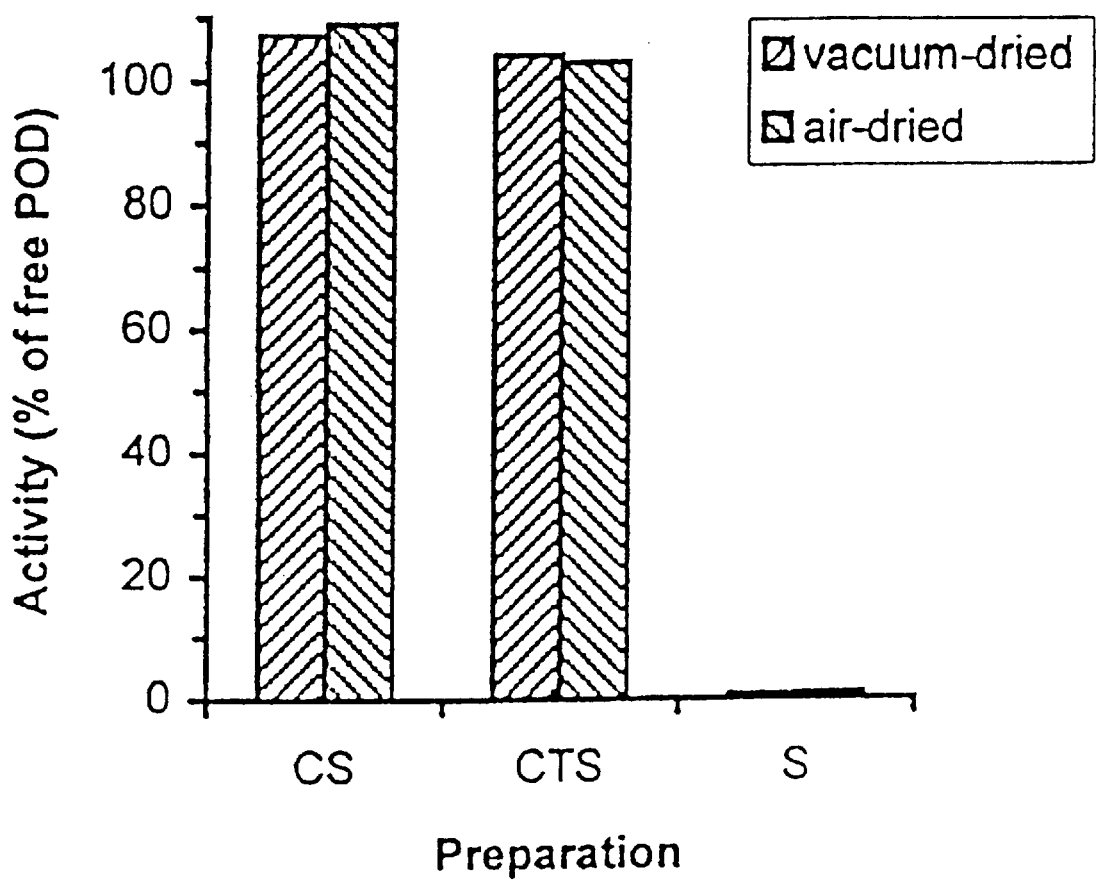
FIG. 4 shows activity of peroxidase (POD) intercalated in montmorillonite in which sodium ions have been replaced with alkylammonium ions (CTS); POD intercalated in montmorillonite in which sodium ions have not been replaced (CS); and POD entrapped in silicate sol-gel matrix (S). Comparison of the foregoing compositions treated either by vacuum drying (lines slanting upward from left to right) or air drying (lines slanted downward from left to right) is also shown.

Intercalative immobilization of POD was very effective as the activity of POD immobilized in the crosslinked phyllosilicate was much higher than that of the simple sol-gel entrapment (FIG. 4). The activity of free POD was measured as 98.2 $\mu$mol guaiacol min$^{-1}$ mg$^{-1}$. The ratio of phyllosilicate suspension to TMOS was 5:1 (v/v).

Figure 5:
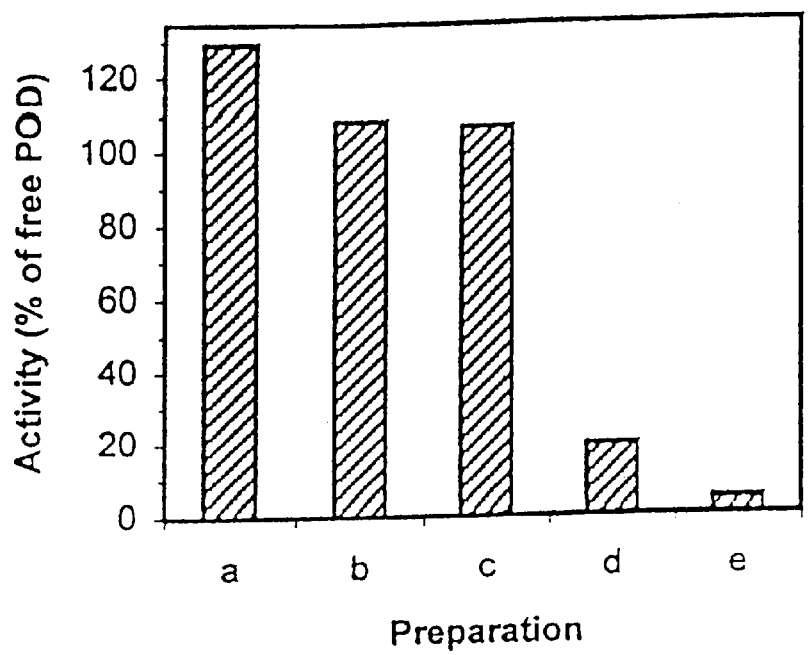
FIG. 5 shows activity of POD immobilized in phyllosilicates (a) Na-phyllosilicate≦0.5 µm fraction; (b) Na-phyllosilicate≦2 µm fraction; (c) trimethylammonium (TMA)-phyllosilicate≦2 µm fraction; (d) cetyltrimethylammonium (HDTMA)-phyllosilicate≦2 µm fraction; (e) activity of POD immobilized in simple sol-gel matrix.

Shown in FIG. 5 is the activity of POD immobilized in differently treated phyllosilicates. The activity of free POD was measured as 98.2 $\mu$mol guaiacol min$^{-1}$ mg$^{-1}$. For Na-phyllosilicate, the activity of POD immobilized in the fine particle-size fraction ($\leq 0.5$ $\mu$m) was higher than that in the larger particle-size fraction ($\leq 2$ $\mu$m). The particle size of phyllosilicates affects their dispersion in aqueous media (Van Olphen, H. [1977] *An introduction to clay colloid chemistry*, 2$^{nd}$ Ed., pp. 1–56, John Wiley & Sons, New York). The fraction of particle size$\leq 0.5$ $\mu$m was more dispersed that the $\leq 2$ $\mu$m fraction in the solutions with same conditions. SEM images showed that the POD-phyllosilicate composite formed with the $\leq 0.5$ $\mu$m fraction exhibited a more uniform pore network than that formed with the $\leq 2$ $\mu$m fraction. For the same particle-size ($\leq 2$ $\mu$m) fraction, surface cations showed significant effect on the activity of intercalatively immobilized POD (FIG. 5). The activity of POD immobilized in TMA-phyllosilicate was a little lower than that in Na-phyllosilicate, while the activity of POD immobilized in HDTMA-phyllosilicate was much lower. One of the explanations may be the effect of surface cations on the dispersion of phyllosilicates in aqueous solution. With TMA replacing Na$^+$ on the surface, phyllosilicate dispersion in aqueous solution decreased as TMA was less hydrated than Na$^+$, which resulted in a heterogeneous pore size in enzyme-phyllosilicate composite. The hydrophobicity of phyllosilicate increased because of TMA on the surface. Unlike lipoxygenase which favored an environment with hydrophobic-hydrophilic balance, POD showed no preference to hydrophobicity (Theng, B. K. G. [1979] *Formation and properties of clay-polymer complexes*, pp. 37–61, Elsevier, New York). As a result, the activity of immobilized POD was affected by TMA replacement of Na$^+$ on phyllosilicate surfaces. HDTMA contains much more hydrophobic groups than TMA. The replacement of Na$^+$ by HDTMA on the surface caused a great reduction in phyllosilicate dispersion because of strong hydrophobic attraction. Phyllosilicate aggregation restricted enzyme intercalation and limited substrate diffusion, resulting in a low activity of the POD-phyllosilicate with HDTMA.

Figure 6:
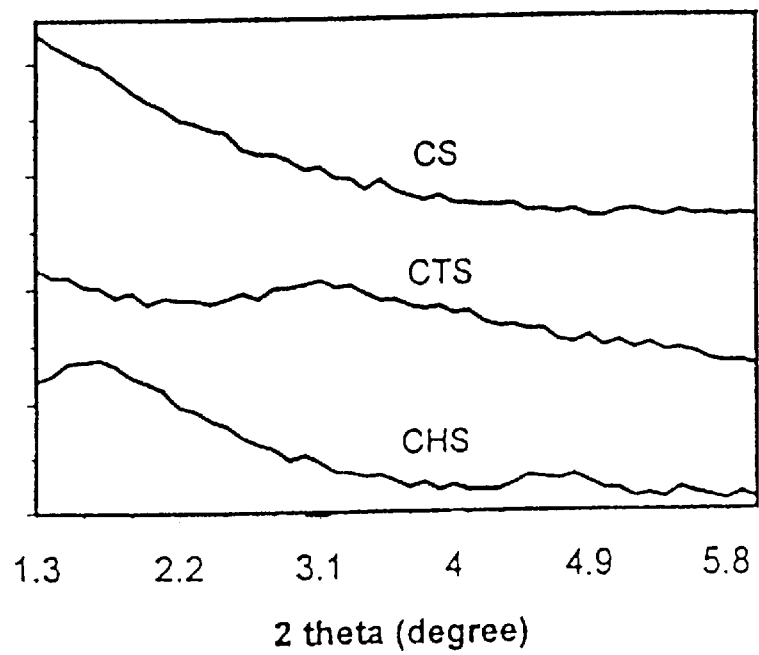
FIG. 6 shows X-ray diffraction patterns of enzyme-phyllosilicate composites (≦2 µm fraction of phyllosilicate SWy-1 with different cations): CS-Na-phyllosilicate; CTS-TMA-phyllosilicate and CHS-HDTMA-phyllosilicate.

The X-ray diffraction pattern of the enzyme-phyllosilicate composite with Na-phyllosilicate was featureless (FIG. 6).

The featureless pattern suggests that the Na-phyllosilicate was fully dispersed in aqueous solution, which is a favorite condition for enzyme intercalation. The enzyme-phyllosilicate composite with TMA-phyllosilicate showed broad and weak peaks in the range of 2θ=2.5 to 4.0° in its X-ray spectra, indicating a few partially fluctuated phyllosilicate aggregates with spacing between 23–35 Å. The X-ray diffraction pattern of the enzyme-phyllosilicate composite with HDTMA-phyllosilicate showed an intense peak around 2θ32 1.7°, indicating fully fluctuated phyllosilicate aggregates with spacing of about 54 Å. Generally aggregates reduced the space of phyllosilicate galleries for enzyme intercalation. That is probably the most important reason for the low activity of POD immobilized in HDTMA-phyllosilicate (FIG. 5d). The reduction of phyllosilicate galleries was insignificant for TMA-phyllosilicate as the activity of POD immobilized in TMA-phyllosilicate was similar to that in Na-phyllosilicate. The ratio of phyllosilicate suspension to TMOS was 5:1 (v/v).

Figure 7:
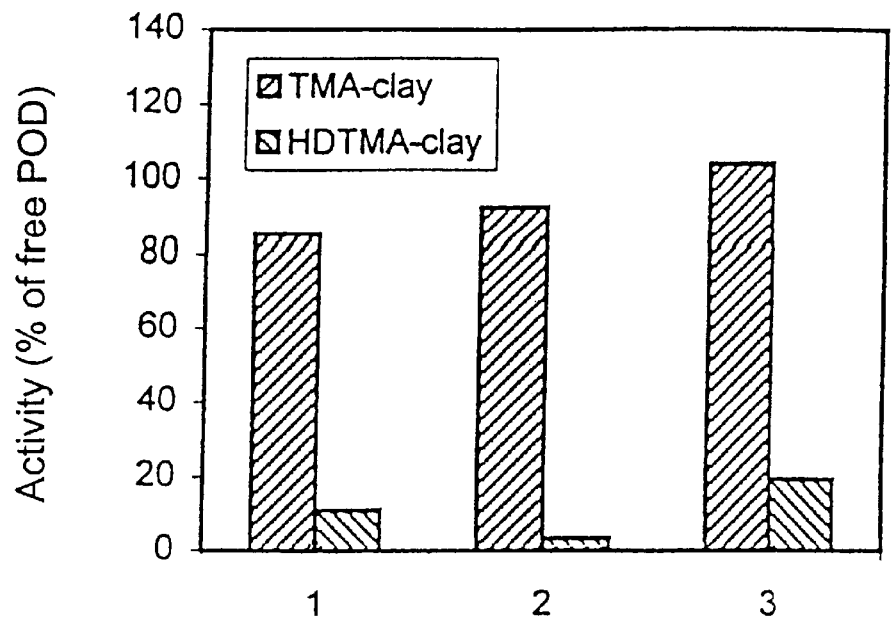
FIG. 7 shows activity of POD immobilized in crosslinked phyllosilicate SWy-1 with different amounts of TMA or HDTMA: (1) smaller than the cation exchange capacity (CEC) of SWy-1; (2) equal to the CEC of SWy-1; and (3) larger than the CEC of SWy-1.

Various amounts of TMA or HDTMA were used to occupy exchange sites of the phyllosilicate. The amounts of TMA and HDTMA used were smaller than, equal to, or larger than the cation exchange capacity (CEC) of SWy-1. The activity of immobilized POD increased with the increasing amount of TMA on the phyllosilicate surface (FIG. 7). The ratio of phyllosilicate suspension to TMOS was 5:1 (v/v). The activity of free POD was measured as 98.2 guaiacol $min^{-1}$ $mg^{-1}$. The activity of immobilized POD was the lowest when the amount of HDTMA added was equal to the CEC of SWy-1. HDTMA contains a long carbon chain and behaves similar to polymers on phyllosilicate surfaces. Added in moderate amount, HDTMA caused phyllosilicate flocculation, while a large amount of HDTMA caused steric stabilization of phyllosilicate suspension and a small amount of HDTMA caused sensitization. The amount of TMA or HDTMA added affected the phyllosilicate dispersion which is one of the important factors in intercalative immobilization of enzymes.

Figure 8:
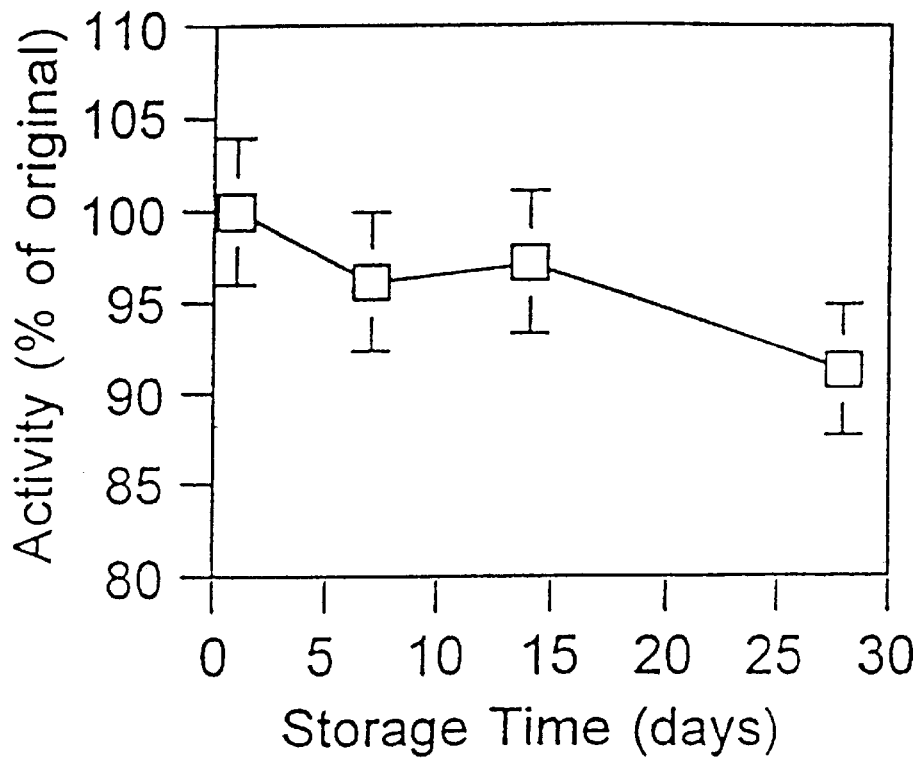
FIG. 8 shows storage stability of POD immobilized in Na-phyllosilicate.

The intercalatively immobilized POD compositions using a ratio of phyllosilicate suspension to TMOS of 5:1 (v/v) were stored without buffer solution at room temperature for four weeks. The activity of intercalatively immobilized POD decreased 5% in the first week and remained similar in the second week (FIG. 8). The original activity of immobilized POD was 107.7 μmol guaiacol $min^{-1}$ $mg^{-1}$. After four weeks of storage, the residual activity of the immobilized POD was about 90% of the original activity. The half-life of intercalatively immobilized POD was estimated to be 169 days by extrapolating the results with regression analysis.

TABLE 3

Relative activity (% of free enzyme*) of POD immobilized in the crosslinked phyllosilicates at various volume ratios ($R_v$) of phyllosilicate (SWy-1) suspension to TMOS (v/v).

| $R_v$ | 10 | 5 | 2.5 | 1 |
|---|---|---|---|---|
| Weight ratio of TMOS to SWy-1 | 6.25 | 12.5 | 25 | 62.5 |
| molar ratio of water to silane (TMOS) | 84 | 42 | 21 | 8.5 |
| CS# | 128.5 | 109.7 | 84.2 | 14.3 |
| CTS# | 136.7 | 104.9 | 67.5 | 17.7 |
| CHS# | 42.5 | 19.6 | 8.2 | 2.2 |

*The activity of free POD was measured as 98.2 μmol guaiacol $min^{-1}$ $mg^{-1}$.
POD immobilized in crosslinked Na-phyllosilicate, CS; in TMA-phyllosilicate, CTS; or in HDTMA-phyllosilicate, CHS.

As shown by the above examples and test results, it is possible, with the present invention, to produce an immobilized biological protein such as an enzyme with activity comparable to or better than that of the free enzyme, and providing advantages of storage stability and reusability. The embodiments described herein are merely exemplary and changes and modifications in the specifically described embodiments can be carried out by one skilled in the art without departing from the scope of the invention. All such changes and modifications are intended to be included within the scope of the invention as defined in the appended claims.

What is claimed is:

1. A composition comprising an active, immobilized bioactive protein comprising:
    (a) a phyllosilicate;
    (b) a bioactive protein intercalated into galleries of said phyllosilicate; and
    (c) a crosslinking compound crosslinking said phyllosilicate and said bioactive protein.

2. The composition of claim 1 wherein said phyllosilicate is montmorillonite.

3. The composition of claim 1 wherein said phyllosilicate comprises sodium ions.

4. The composition of claim 1 wherein said phyllosilicate comprises alkylammonium ions.

5. The composition of claim 1 wherein said bioactive protein is an enzyme selected from the group consisting of lipoxygenase, peroxidase, trypsin, acid phosphatase, β-glucosidase, lipase, alkaline phosphatase, hydroxylase, reductase, superoxide dismutase, albumin, and cell-bonded enzymes.

6. The composition of claim 1 wherein said crosslinking compound is selected from the group consisting of tetramethyl orthosilicate, tetraethoxy silicate, propyltrimethoxy silicate, polydimethylortho silicate and methyltrimethoxy silicate.

7. The composition of claim 1 having a macroporous structure.

8. The composition of claim 6 sufficiently hydrated to substantially maintain said macroporous structure.

9. The composition of claim 1 having a volume ratio of about 1 to about 3 weight % aqueous suspension of phyllosilicate to crosslinking agent of at least about 1:1.

10. The composition of claim 9 wherein said ratio is at least about 5:1.

11. A composition comprising an active, immobilized enzyme comprising:
    (a) montmorillonite comprising ions selected from the group consisting of sodium and alkylammonium ions;
    (b) an enzyme selected from the group consisting of lipoxygenase, peroxidase, trypsin, acid phosphatase, β-glucosidase, lipase, alkaline phosphatase, hydroxylase, reductase, superoxide dismutase, albumin, and cell-bonded enzymes intercalated into the galleries of said montmorillonite; and
    (c) tetramethoxysilane crosslinking said enzyme and said montmorillonite, said composition having been made using a volume ratio of montmorillonite suspension of about 1 to about 3 weight % to tetramethoxysilane of at least about 1:1 to obtain said composition.

12. A method of making a composition comprising an active, immobilized bioactive protein comprising:
    (a) delaminating a sodium-saturated phyllosilicate;
    (b) mixing said bioactive protein with said phyllosilicate;
    (c) crosslinking said phyllosilicate and said bioactive protein with a crosslinking compound.

13. The method of claim 12 wherein said phyllosilicate is montmorillonite.

14. The method of claim 12 wherein said delaminated phyllosilicate is saturated with sodium ions prior to mixing with said bioactive protein.

15. The method of claim 14 wherein said sodium ions in said delaminated phyllosilicate are replaced with alkylammonium ions.

16. The method of claim 12 wherein said bioactive protein is an enzyme selected from the group consisting of lipoxygenase, peroxidase, trypsin, acid phosphatase, β-glucosidase, lipase, alkaline phosphatase, hydroxylase, reductase, superoxide dismutase, albumin, and cell-bonded enzymes.

17. The method of claim 12 wherein said crosslinking compound is selected from the group consisting of tetramethyl orthosilicate, tetraethoxy silicate, propyltrimethoxy silicate, polydimethylortho silicate and methyltrimethoxy silicate.

18. The method of claim 12 further comprising:

(d) vacuum drying the composition of step (c).

19. The method of claim 18 further comprising:

(e) grinding the dried composition of step (d).

20. A method of making a composition comprising an active, immobilized enzyme comprising:

(a) delaminating a montmorillonite;

(b) saturating said delaminated montmorillonite with sodium ions;

(c) mixing an enzyme selected from the group consisting of lipoxygenase, peroxidase, trypsin, acid phosphatase, and β-glucosidase, with said montmorillonite of step (b) whereby said enzyme becomes intercalated into the galleries of said montmorillonite;

(d) mixing tetramethyl orthosilicate with said montmorillonite from step (c) to form a mixture having a ratio of montmorillonite to tetramethyl orthosilicate of at least about 5:1;

(e) allowing said mixture from step (d) to crosslink; and (f) drying said crosslinked mixture from step (e) by means not destructive to macropores in said mixture.

21. The method of claim 20 further comprising replacing sodium ions in said delaminated montmorillonite of step (a) with alkylammonium ions.

* * * * *